United States Patent [19]

Chikama

[11] 4,281,931
[45] Aug. 4, 1981

[54] MEASURING APPARATUS COMPRISING LIGHT OPTICS UTILIZING CYLINDRICAL FOCUSING GLASS FIBER

[75] Inventor: Toshio Chikama, Tokyo, Japan

[73] Assignee: Machida Endoscope Co., Ltd., Tokyo, Japan

[21] Appl. No.: 968,025

[22] Filed: Dec. 11, 1978

[30] Foreign Application Priority Data

Dec. 21, 1977 [JP] Japan ............................ 52/171115[U]
Nov. 2, 1978 [JP] Japan ............................ 53/151380[U]
Nov. 2, 1978 [JP] Japan ............................ 53/151381[U]

[51] Int. Cl.$^3$ ............................................. G01B 11/00
[52] U.S. Cl. ..................... 356/372; 350/96.18; 356/375
[58] Field of Search ............... 356/372, 138, 73.1, 356/153, 241; 350/190, 96.18, 96.31, 296, 433; 362/350, 296

[56] References Cited

U.S. PATENT DOCUMENTS

| | | | |
|---|---|---|---|
| 2,316,301 | 4/1943 | Ullman | 362/32 |
| 3,187,185 | 6/1965 | Milnes | 356/1 |
| 3,733,138 | 5/1973 | Weinberg | 356/241 |
| 3,964,824 | 6/1976 | Dixon | 350/190 |
| 4,021,217 | 5/1977 | Bondybey et al. | 356/73.1 |
| 4,184,748 | 1/1980 | Kugler et al. | 350/190 |

FOREIGN PATENT DOCUMENTS 2650023  5/1978  Fed. Rep. of Germany ........ 350/96.18

OTHER PUBLICATIONS

Uchida et al., "Optical Characteristics of a Light Focusing Fiber Guide & its Applications," IEEE. J. R. Quantum Electronics, 10-1970, pp. 606-612.
Crow et al., "GaAs Laser Array Source Package", Optics Letters, 7-1977, pp. 40-42.
Smithgall et al., "High Speed Fiber-Diameter Measurements Using Forward Light Scattering", App. Optics, 9-1977, pp. 2395-2402.

*Primary Examiner*—William H. Punter
*Attorney, Agent, or Firm*—Peter L. Berger

[57] ABSTRACT

The present invention discloses herewith measuring apparatus for measuring the dimension of an object or the distance to said object, said measuring apparatus utilizing an optical characteristic of a focusing glass fiber, a line or a circle or a focus being indicated on said object. The invention comprises a rod lens composed of said focusing glass fiber of suitable length, a non-diffusive light beam, for example a laser beam, being fed to the radial side of said rod lens, said light beam being scattered radially by said rod lens, said scattered light beam being applied to said object directly or by way of reflecting means, and a line or a circle or a focus is indicated on said object. By these provisions, the dimension of the object, for example a cancer in a body cavity, can be easily measured in order to observe time transfiguration of said cancer. In addition, the distance to bleeding position can be correctly measured in order to adjust an output of a laser surgical instrument.

23 Claims, 16 Drawing Figures

MEASURING APPARATUS COMPRISING LIGHT OPTICS UTILIZING CYLINDRICAL FOCUSING GLASS FIBER

BACKGROUND OF THE INVENTION

A. Field of the Invention

The present invention relates generally to measuring apparatus for measuring an object with an endoscope, for example a cancer in a body cavity or a flaw in a reacting pile, the innerside of those cannot be measured directly, or more particularly, to measuring apparatus which utilizes an optical characteristic of focusing glass fiber in order to indicate a line or a circle or a focus on said object.

B. Description of the Prior Art

An endoscope is an optical instrument for inspecting a cancer or a bleeding point in a body cavity or a flaw in a reacting pile, comprising an observing optical means such as an optical fiber bundle or a relay lens system, an image of the object caught at a forward portion of the endoscope being observed at an eyepiece portion of a grip.

Measuring tools or instruments can not be inserted into abovesaid body cavity or reacting pile in order to directly measure the dimension of the object therein or a distance thereto.

But, many advantages will surely be obtained if the measurement is possible. For example, measurement of the dimension of a cancer will lead into observation of time transfiguration of it. In addition, measurement of the distance to bleeding point will also lead into the possibility of adjusting an output of a laser beam when conducting laser surgery. With all these advantages, we can not find the pertinent prior art in this technical field.

SUMMARY OF THE INVENTION

A focusing glass fiber is an uniform glass fiber whose refractive index varies continuously in a radial direction, the glass fiber itself having convergency equivalent to that of a lens, and recently is used for optical communication means. A rod lens is cut out of the focusing glass fiber of suitable length. When a non-diffusive light beam, for example a laser beam, is fed to the radial side of said rod lens, said light beam is scattered radially by said rod lens. Accordingly, an optical display will be obtained on a object by guiding said scattered light beam directly or by way of reflective means on the object.

The present invention aims at measuring apparatus for measuring the dimension of the object or the distance to said object, said measuring apparatus utilizing an optical characteristic of the focusing glass fiber, a line or a circle or a focus being indicated on said object. The invention comprises the rod lens composed of said focusing glass fiber of suitable length, a non-diffusive light beam, for example a laser bem, being fed to the radial side of said rod lens, said light beam being scattered radially by said rod lens, said scattered light beam being applied to said object directly or by way of reflecting means, and a line or a circle or a focus is indicated on said object.

The first object of the invention is to measure the dimension of the object by indicating a plurality of lines on the object. To this end, a plurality of rod lenses and light guide means are provided at predetermined intervals.

The second object of the invention is to measure the dimension of the object by indicating a circle on the object. To this end, a conical mirror with an axial symmetric reflector is used for reflective means, a rod lens being stood upright at the center of said conical mirror, a light beam fed by light guide means being scattered radially by said rod lens.

The third object of the invention is to measure the distance to the object by indicating a focus on the object. To this end, a bowl-like mirror with an axial symmetric reflector is used for reflective means, the rod lens being stood upright at the center of said bowl-like mirror, a light beam fed by the light guide means being scattered radially by said rod lens.

The above- and further objects of the invention will more fully appear from the following detailed description when the same is read in connection with the accompanying drawings. It is to be expressly understood, however, that the drawings are for purpose of illustration only and are not intended as a definition of the invention.

DETAILED DESCRIPTION OF PREFERRED EMBODIMENTS

The fundamental novel feature of the present invention lies in the utilization of optical characteristic of a focusing glass fiber.

Figure 1:
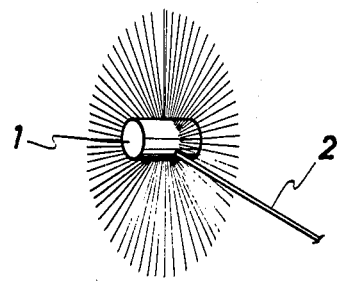
FIG. 1 is a schematic illustration showing an optical characteristic of a focusing glass fiber.

In FIG. 1, numeral 1 indicates a rod lens composed of the focusing glass fiber of suitable length. When a non-diffusive light beam, for example a laser beam, is fed to the radial side of the rod lens 1 by way of light guide means 2 of optical fiber bundles, said light beam is scattered radially from the circumference of the enlightened point.

Figure 2:
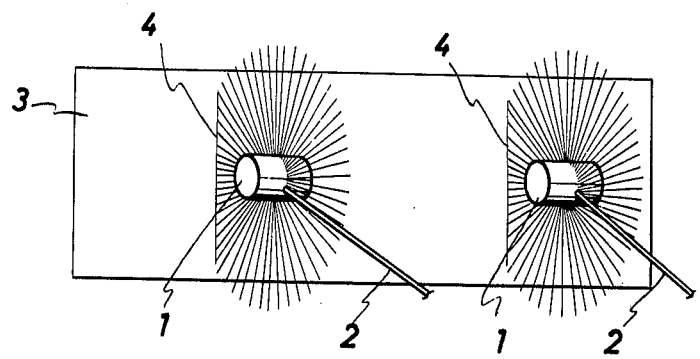
FIG. 2 is a schematic illustration showing a first embodiment according to the invention.

In FIG. 2, there is shown a first embodiment of the present invention. A plurality of rod lenses 1 and light guide means 2 are provided at predetermined intervals and a plurality of lines 4 are indicated on the object 3. The dimension of the object 3 can be measured by comparing the intervals with the object 3. A plurality of light guide means 2 may be provided at one rod lens 1 at predetermined intervals.

Figure 3:
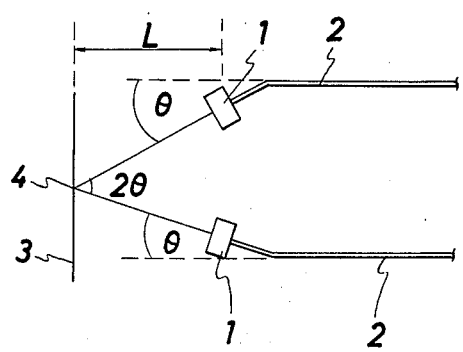
FIG. 3 is a schematic illustration showing another embodiment according to the invention.

In FIG. 3, there is shown another embodiment of the invention. Two sets of rod lenses 1 and the light guide means 2 are provided at predetermined or variable angle $\theta$ in order to indicate a line 4 on the object 3. The distance L to the object 3 can be measured by taking the angle $\theta$, because the interval of each rod lens 1 is fixed.

Figure 4:
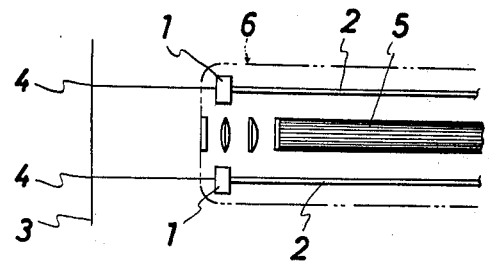
FIG. 4 is a schematic illustration showing an endoscope to which is applied the first embodiment according to the invention.

In FIG. 4, there is shown an endoscope to which is applied the present embodiment. Two sets of rod lenses 1 and light guide means 2 are provided at predetermined intervals at a forward portion 6 of the endoscope in which is housed observing optical means 5 or so on. Lines 4 of the predetermined intervals are indicated on the object 3 in a body cavity, when the endoscope is inserted and the light beam is scattered by the rod lens 1. Consequently, the dimension of the object such as a cancer can be measured. In addition, the distance L to the object 3 can be measured by taking the angle $\theta$. Further, the location of the object 3 in the body cavity can be seen by taking photographs with the line 4.

Figure 5:
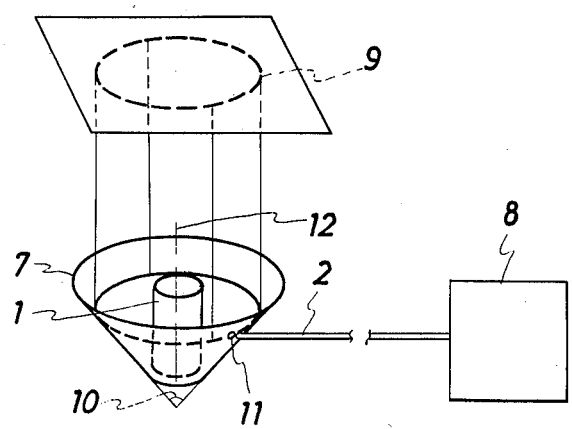
FIG. 5 is a schematic illustration showing a second embodiment according to the invention.

In FIG. 5, there is shown a second embodiment of the invention. A conical mirror 7 with an axial symmetric reflector is used for the reflecting means. A rod lens 1 is provided upright at the center of said conical mirror 7, so that its axis is substantially orthogonal to the surface on which object 3 is located. A light beam fed by light guide means 2 from a light source 8 is scattered radially by said rod lens 1 in order to change the light beam into a circle 9. Said conical mirror is reflective means for changing the radially scattered light beam to a circle 9. The vertical angle 10 of the conical mirror 7 has 90 degrees. A light guide aperture 11 may be provided to the conical mirror 7, or a part of the conical mirror 7 may be composed of a semipermeable mirror in order to lead the light beam therefrom, or a part pf the conical mirror 7 may be left transparent in order to lead the light beam therefrom. The conical mirror 7 is not necessarily needed for its whole circumference, namely, a part of it may be cut away. In such case, the circle 9 lacks a part of it.

In operation, a light beam generated by the light source 8 is fed to the rod lens 1 by way of light guide means 2 and the light beam is then scattered radially to the circumference of enlightened point by the rod lens 1. Said scattered light beam comes to the inner surface of the conical mirror 7 and then is reflected to the direction of the optical axis 12 of the rod lens 1, because the vertical angle 10 of the conical mirror 7 has 90 degrees to set the angle of incidence at 45 degrees. Finally, the circle 9 of standard diameter D is indicated on the object 3. Said standard diameter D is fixed regardless of the distance L to the object 3.

Figure 6:
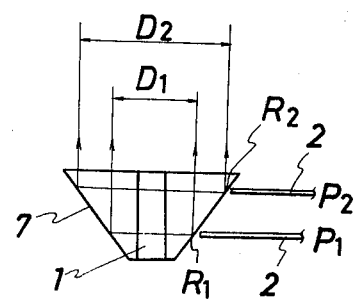
FIG. 6 is a schematic illustration showing another embodiment according to the invention.

In FIG. 6, the diameter D of the circle 9 is variable. The relationship between the position P of the light beam fed by light guide means 2 and reflecting position R of the conical mirror 7 is varied by suitable means. In case that the light beam is fed from the position P1, said light beam is scattered radially by the rods lens 1 and reflected at position R1 of the conical mirror 7, finally indicating the circle 9 of D1 diameter on the object 3. In the same manner, in case that the light beam is fed from the position P2, said light beam is scattered radially by the rod lens 1 and reflected at position R2 of the conical mirror 7, finally indicating the circle 9 of D2 diameter on the object 3. The circle 9 of desired diameter can thus be indicated on the object 3 in order to compare the circle 9 with the object 3. For this reason, the dimension of the object 3 can be measured by calculating beforehand the relationship between the position P and the diameter D of the circle 9.

By the way, foregoing embodiments concern the case in which the object 3 is not inclined to the optical axis 12 of the rod lens 1, but the present invention is also applicable even if the object 3 has an inclination or is at an angle with respect to the optical axis 12.

Figure 7:
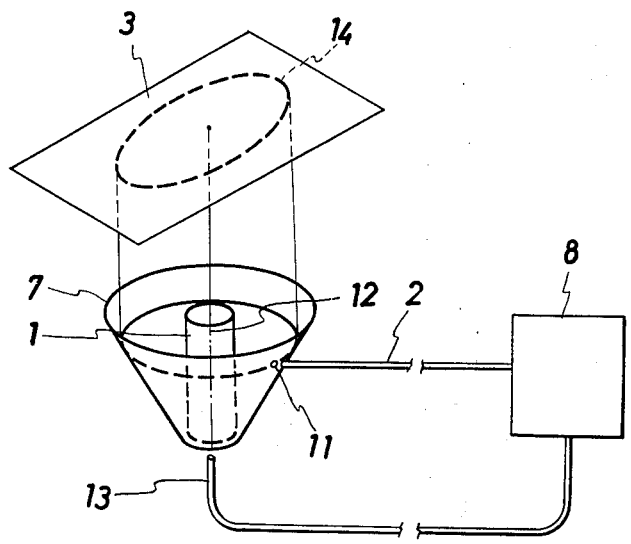
FIG. 7 is a schematic illustration showing an embodiment which is also applicable to an inclined object.
Figure 8:
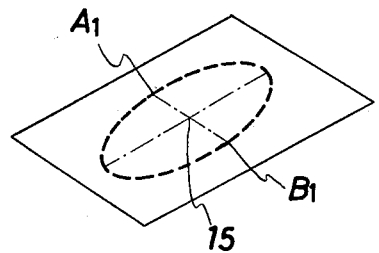
FIG. 8 is a explanatory view of FIG. 7.

In FIG. 7, a center indicating light 13 is fed to the direction of the optical axis 12 of the rod lens 1. In an ellipse 14 in FIG. 8, points A1 and B1 indicate a standard dimension which are situated at an equivalent distance from the center 15 as well as being symmetric thereto.

Figure 9:
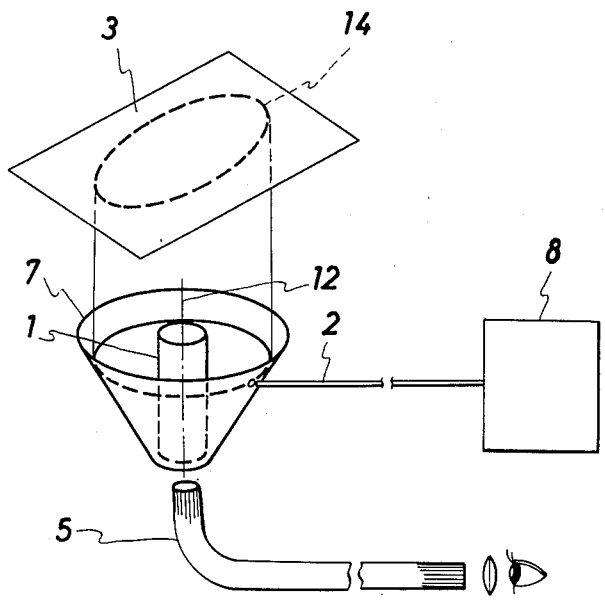
FIG. 9 is a schematic illustration showing another embodiment according to the invention.
Figure 10:
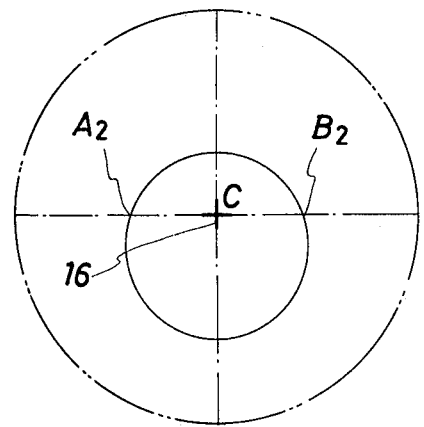
FIG. 10 is an explanatory view of FIG. 9.

In FIG. 9, the optical axis 12 of the rod lens 1 is in accord with the center C of the visual field of the observing optical means 5. Points A2 and B2 in FIG. 10 indicate a standard dimension which are situated at an equivalent distance from the center C as well as symmetric thereto. Measuring error can be decreased by the present embodiment, because a parallax does not occur. A mark 16 may be put on at the center C of the visual field.

Figure 11:
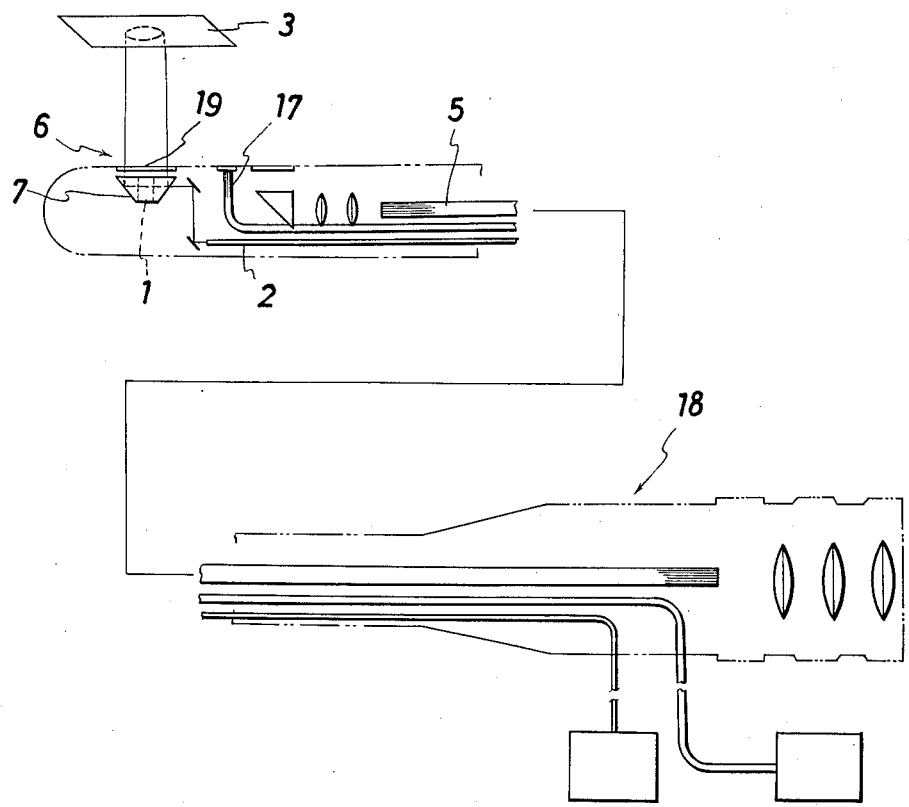
FIG. 11 is a schematic illustration showing an endoscope to which is applied the second embodiment according to the invention.

FIG. 11 is a schematic illustration showing an endoscope to which is applied the present embodiment, comprising a light guide 17 for illuminating the object 3, observing optical means 5 for transmitting an image of the object 3 to a grip portion 18, light guide means 2 composed of a laser guide and a mirror, the rod lens 1, the conical mirror 7, a window 19 for sending out the light beam from the forward portion 6 of the endoscope.

By these provisions, the measurement of a cancer in a body cavity or a flaw in a reacting pile is possible by comparing the circle with these objects which can not be measured directly.

Figure 12:
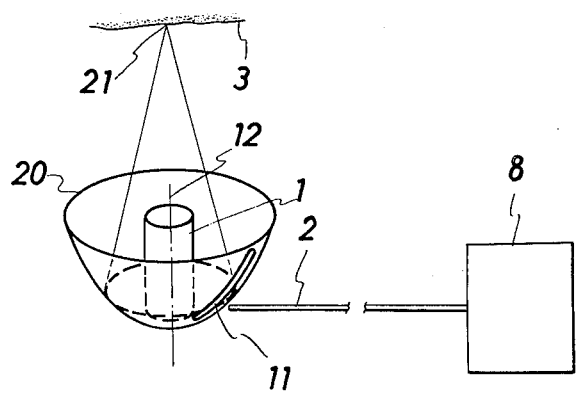
FIG. 12 is a schematic illustration showing a third embodiment according to the invention.

In FIG. 12, there is shown the third embodiment of the invention. A bowl-like mirror 20 with an axial symmetric reflector is used for reflective means, a rod lens 1 being stood upright at the center of said bowl-like mirror 20, a light beam fed by the light guide means 2 from the light source 8 being scattered radially by said rod lens 1, and a focus point 21 is indicated on the object 3 in order to measure the distance to said object 3. Said bowl-like mirror 20 is the reflective means for bringing a radially scattered beam light into a focus point 21 on the object 3. The shape of the bowl-like mirror 20 may be hemispherical, parabolic, spheroid, conical or horn-shaped. A light guide aperture 11 may be provided to the bowl-like mirror 20, or a part of the bowl-like mirror 20 may be composed of a semipermeable mirror in order to lead the light beam therefrom, or a part of it may be transparent in order to lead the light beam therefrom. The bowl-like mirror 20 is not necessarily needed for its whole circumference, namely, a part of it may be cut away.

Figure 13:
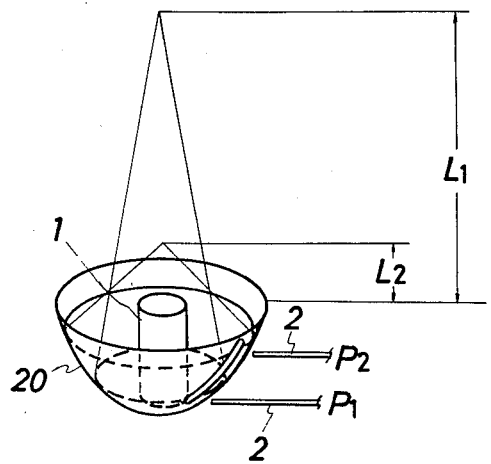
FIG. 13 is an explanatory view of FIG. 12.

In operation, the non-diffusive light beam such as a laser beam from the light source 8 is fed to the radial side of the rod lens 1 by way of light guide means 2 and then scattered radially by the rod lens 1. Said scattered light beam is then reflected by the bowl-like mirror 20 to the direction of the optical axis 12 of the rod lens 1, finally bringing into a focus point 21 on the object 3. The distance L to the object 3 can be measured by calculating beforehand the relationship between the positions P1, P2 and the distance L1, L2. This is seen in FIG. 13.

Figure 14:
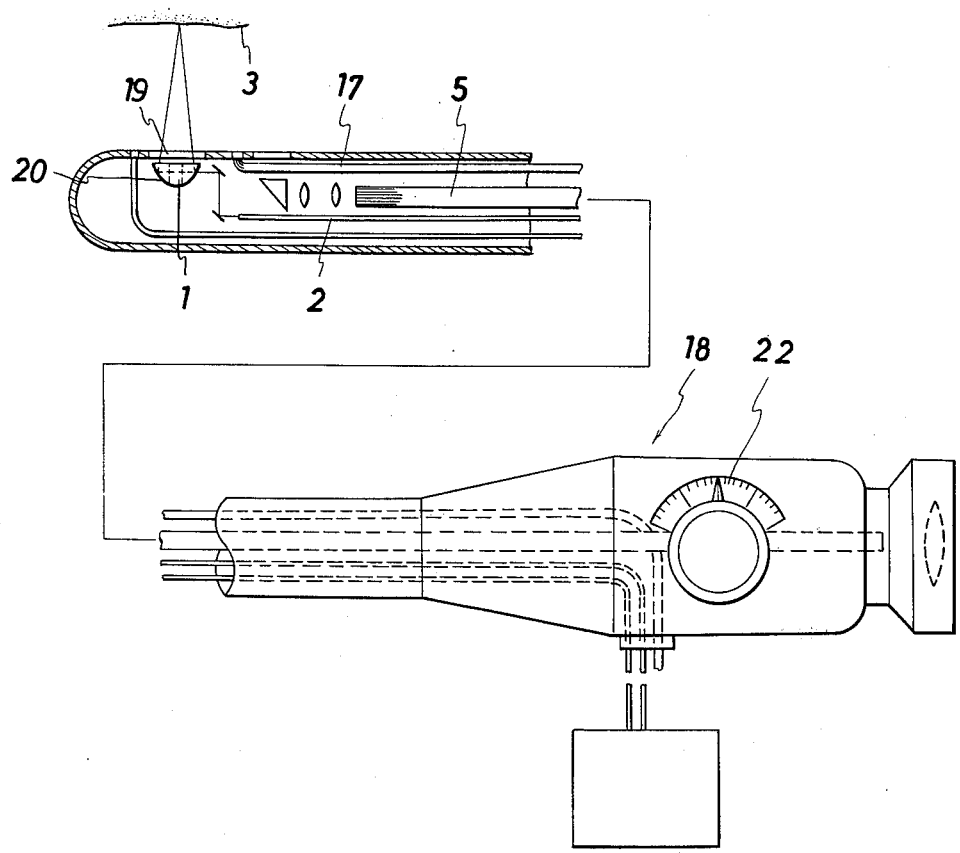
FIG. 14 is a schematic illustration showing a side-view type endoscope to which is applied the third embodiment according to the invention.
Figure 15:
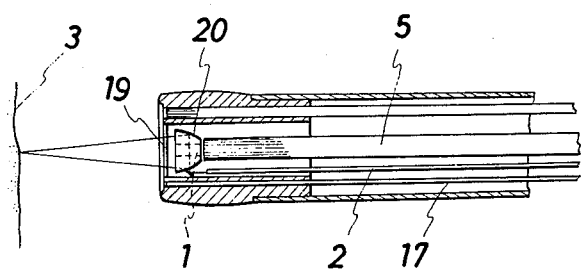
FIG. 15 is a schematic illustration showing a forward-view type endoscope to which is applied the third embodiment according to the invention.

FIGS. 14 and 15 are schematic illustrations showing a side-view type and a forward-view type endoscope to which are applied the present embodiment, comprising a light guide 17 for illuminating the object 3, an observing optical means 5 for transmitting an image of the object 3 to the grip portion 18, light guide means 2 composed of a laser guide and a mirror, the rod lens 1, the bowl-like mirror 20, a window 19, indicating means 22 such as a dial plate for showing the result of the measurement.

Figure 16:
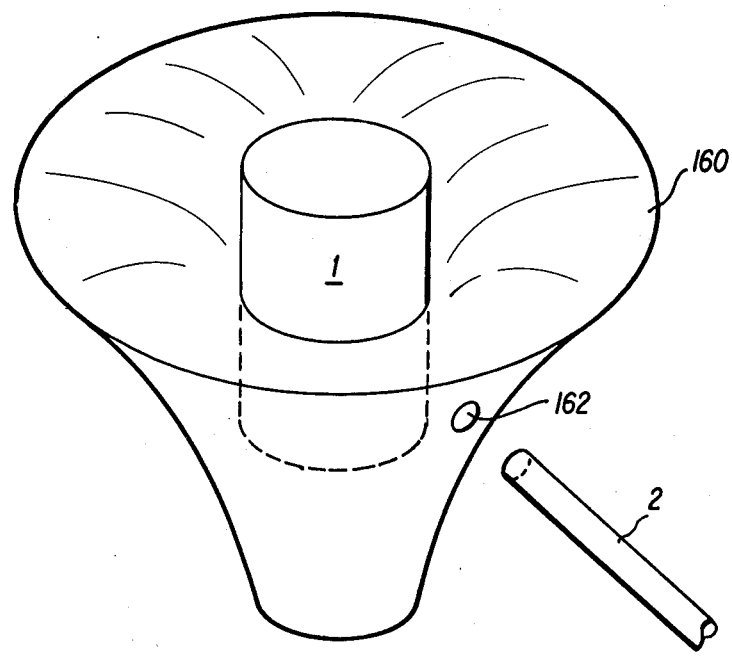
FIG. 16 is a schematic illustration of a horn-shaped reflector used with this invention.

FIG. 16 shows yet another embodiment of this invention with a bowl-shaped reflector 160 formed of a bowl-shaped mirror having an aperture 162 similar to aperture 11 of FIG. 5. The rod lens 1 is placed similarly to the rod lens 1 in FIG. 5 as is the light guide means 2.

By these provisions, a focus is indicated on the object, for example a cancer in a body cavity, and the position P is displayed on the indicating means 22 by way of an interlocking means (not shown), thereby the distance D to the object is measured.

As is described in detail, the present invention utilizes an optical characteristics of the focusing glass fiber in order to measure the dimension of the object or a distance thereto, and time transfiguration of a cancer in a body cavity is observed or an out put of a laser surgerical instrument is adjusted by using measuring apparatus according to the invention.

While there have been shown and described and pointed out the fundamental novel features of the invention as applied to preffered embodiments. It will be understood that the various omissions and substitutions and changes in the form and details of the mechanism illustrated and operation may be made by those skilled in the art without departing from the spirit of the invention.

What is claimed is:

1. A measuring apparatus for remotely measuring the size of an object on a surface and/or the distance of said apparatus from said object, said apparatus comprising
   a rod lens comprising a generally cylindrical focusing glass fiber having an axis,
   a non-diffusive light beam and a light guide means for carrying said light beam to said rod lens to intersect with the radial side of said focusing glass fiber radially scattering said light beam,
   said radially scattered light beam impinging on said surface to form a visible light on said surface,
   a housing containing said rod lens located at the distal end thereof toward said object,
   viewing means to view said visible light and said object for said measuring wherein the axis of said rod lens is oriented substantially orthogonal to said surface, further comprising optical means optically coupled to said rod lens, wherein said optical means forms a circle of light, said visible light comprising said circle of light.

2. A measuring apparatus for remotely measuring the size of an object on a surface and/or the distance of said apparatus from said object, said apparatus comprising
   a rod lens comprising a generally cylindrical focusing glass fiber having an axis,
   a non-diffusive light beam and a light guide means for carrying said light beam to said rod lens to intersect with the radial side of said focusing glass fiber rod lens radially scattering said light beam,
   said radially scattered light beam impinging on said surface to form a visible light on said surface,
   a housing containing said rod lens located at the distal end thereof toward said object,
   viewing means to view said visible light and said object for said measuring, wherein the axis of said rod lens is oriented at an angle with respect to said surface,
   further comprising optical means optically coupled to said rod lens, wherein said optical means forming an elliptical visible light on said surface.

3. A measuring apparatus as claimed in claim 1 or 2 wherein said optical means comprises a reflective surface located with respect to said rod lens to direct said light beam toward said surface.

4. A measuring apparatus as claimed in claim 3, wherein said reflective surface comprises a conical mirror with an axial symmetric reflector, said rod lens being stood upright at the center of said conical mirror, radially by said rod lens in order to measure the dimension of said object.

5. Measuring apparatus of claim 4, wherein a light guide aperture is provided on the conical mirror.

6. Measuring apparatus of claim 4, wherein the conical mirror is composed of a semipermeable mirror in order to lead the light beam therefrom.

7. Measuring apparatus of claim 4, wherein a part of the conical mirror is transparent in order to lead the light beam therefrom.

8. Measuring apparatus of claim 4, comprising a center indicating light directed along the optical axis of the rod lens in order to point out the center.

9. Measuring apparatus of claim 4, wherein the optical axis of the rod lens is aligned with the center of the visual field of the viewing means.

10. Measuring apparatus of claim 4, wherein a part of the conical mirror is cut away.

11. A measuring apparatus as claimed in claim 4, comprising means to vary the relationship between the position of the light beam fed by said light guide means and the reflecting position of the conical mirror.

12. A measuring apparatus as claimed in claim 3, further comprising an endoscope housing said measuring apparatus, said endoscope comprising means for providing said viewing means, whereby said visible light can be viewed by the observer of said endoscope.

13. A measuring apparatus as claimed in claim 1, wherein said optical means comprises a reflective surface located optically coupled to said rod lens to direct said radially scattered light beam toward said surface, said rod lens being oriented substantially orthogonally with respect to said surface, said reflective surface focusing said visible light to form a visible spot of light on said surface to measure the distance from said distal end to said object.

14. A measuring apparatus as claimed in claim 13, wherein said reflective surface comprises a bowl-like mirror with an axial symmetric reflector, said rod lens being stood upright at the center of said bowl-like mirror, said light beam fed by the light guide means being scattered radially by said rod lens, whereby said spot of light is focused on the object in order to measure the distance to said object.

15. Measuring apparatus of claim 14, wherein the bowl-like mirror is hemispherical.

16. Measuring apparatus of claim 14, wherein the bowl-like mirror is parabolic.

17. Measuring apparatus, of claim 14, wherein the bowl-like mirror is spheroid.

18. Measuring apparatus of claim 14, wherein the bowl-like mirror is conical.

19. Measuring apparatus of claim 14, wherein the bowl-like mirror is horn-shaped.

20. Measuring apparatus of claim 14, wherein a light guide aperture is provided on the bowl-like mirror.

21. Measuringg apparatus of claim 14, wherein the bowl-like mirror is composed of a semipermeable mirror.

22. Measuring apparatus of claim 14, wherein a part of the reflector of the bowl-like mirror is transparent in order to lead the light beam therefrom.

23. Measuring apparatus of claim 14, wherein a part of the bowl-like mirror is cut away.

* * * * *